US012685495B1

(12) United States Patent
Sukkau et al.

(10) Patent No.: US 12,685,495 B1
(45) Date of Patent: Jul. 21, 2026

(54) MU-MAP ALIGNMENT USING CAD DATA

(71) Applicant: Siemens Medical Solutions USA, Inc.,
Malvern, PA (US)

(72) Inventors: Johann Sukkau, Herzogenaurach (DE);
Noah Birge, Knoxville, TN (US);
Rainer Kurth, Erlangen (DE); **Vincent
Kelber**, Bamberg (DE)

(73) Assignee: Siemens Medical Solutions USA, Inc.,
Malvern, PA (US)

( * ) Notice: Subject to any disclaimer, the term of this
patent is extended or adjusted under 35
U.S.C. 154(b) by 0 days.

(21) Appl. No.: 19/184,489

(22) Filed: Apr. 21, 2025

(51) Int. Cl.
*A61B 6/03* (2006.01)
*A61B 6/00* (2024.01)
*A61B 6/42* (2024.01)

(52) U.S. Cl.
CPC .............. *A61B 6/032* (2013.01); *A61B 6/037*
(2013.01); *A61B 6/4241* (2013.01); *A61B
6/5235* (2013.01)

(58) Field of Classification Search
CPC ...................................................... A61B 6/037
See application file for complete search history.

(56) References Cited

U.S. PATENT DOCUMENTS

| | | | | |
|---|---|---|---|---|
| 5,875,225 A | * | 2/1999 | Wallschlaeger | ....... A61B 6/032 |
| | | | | 378/15 |
| 11,701,067 B2 | * | 7/2023 | Vija | ...................... A61B 6/037 |
| | | | | 250/363.04 |
| 2007/0131858 A1 | * | 6/2007 | Wollenweber | ......... A61B 6/032 |
| | | | | 250/252.1 |
| 2009/0278049 A1 | * | 11/2009 | Ladebeck | ............ G01R 33/481 |
| | | | | 250/361 R |
| 2011/0317900 A1 | * | 12/2011 | Pal | ........................... A61B 6/58 |
| | | | | 702/108 |
| 2015/0087958 A1 | * | 3/2015 | Kartmann | ............ G01R 33/481 |
| | | | | 600/411 |
| 2016/0069973 A1 | * | 3/2016 | Fenchel | ............... G01R 33/481 |
| | | | | 324/309 |
| 2025/0318791 A1 | * | 10/2025 | Massanes Basi | ...... A61B 6/037 |

* cited by examiner

*Primary Examiner* — Colin T. Sakamoto

(57) ABSTRACT

Systems and methods include acquisition of a respective computed tomography (CT) image of each of a plurality of adjacent portions of a patient support, determination of a respective transformation matrix between each of the CT images and a corresponding portion of a predetermined linear attenuation coefficient map of the patient support, application of the respective transformation matrix to each of the CT images, generation of a respective linear attenuation coefficient map from each of the transformed CT images, combination of the linear attenuation coefficient maps into a combined linear attenuation coefficient map, and reconstruction of a positron emission tomography (PET) image based on PET data and the combined linear attenuation coefficient map.

20 Claims, 14 Drawing Sheets

200

MU-MAP ALIGNMENT USING CAD DATA

BACKGROUND

With Positron Emission Tomography (PET), one can generate quantitative images which represent biological processes (e.g., glucose metabolism, receptor affinity) within a patient. PET images can assist doctors in diagnosing disease, designing treatment plans, and evaluating treatment effectiveness. PET images are particularly useful in the evaluation and staging of cancer, cardiovascular disease and brain disorders.

Typically in PET imaging, a radiotracer is administered to a patient via intravenous injection, inhalation, oral ingestion or direct organ injection. The tracer accumulates at an area of interest (e.g., tumor, heart) based on its composition and affinity. Radioactive decay of the tracer results in the emission of positrons which encounter electrons and are annihilated thereby. An annihilation produces two 511 keV photons which travel in approximately opposite directions.

A ring of detectors surrounds the patient, and a coincidence is identified when two of the detectors detect the arrival of two photons within a short time window indicating that the two photons arose from the same positron annihilation. Because the two "coincident" photons travel in approximately opposite directions, the locations of the two detector crystals define a Line-of-Response (LoR) along which an annihilation may have occurred. PET data represents each detected annihilation as a LoR between two detector crystals. Time-of-flight (TOF) PET data also includes the difference between the detection times of the two photons arising from the annihilation. This difference may be used to estimate a particular position along the LoR at which the annihilation event occurred. The PET data is attenuation-corrected and a three-dimensional PET image is reconstructed from the PET data using known algorithms such as filtered backprojection (FBP) and ordered subsets expectation maximization (OSEM).

PET data is attenuation-corrected based on attenuative characteristics of materials through which the photons pass prior to arrival at the detectors. These materials include the tissues of the patient and any hardware elements which are also present within the ring of detectors, such as a patient table. In the case of PET-Magnetic Resonance (MR) imaging, these hardware elements may also include local MR transmit/receive coils.

The attenuative characteristics are typically represented by one or more maps of linear attenuation coefficients, or mu-maps. A mu-map of the patient may be determined from MR or Computed Tomography (CT) data of the patient. Such an approach is not suitable for PET-MR imaging because MR imaging does not measure electron density but rather relies on the existence of protons within an object to be imaged. Typical clinical MR imaging would therefore not receive signals from hardware elements such as the patient table and MR coils which are located in the PET field of view and which contribute to photon attenuation. Accordingly, MR imaging cannot be used to generate a suitable attenuation correction map corresponding to such hardware elements.

Conventional methods for determining a mu-map of the hardware elements include calculation of the mu-map based on the material composition of the hardware elements and the attenuative characteristics of the materials with respect to 511 keV photons. Such calculated mu-maps are known to be inaccurate and poorly reflect the attenuative complexities of the hardware elements. Alternatively, a hardware element mu-map may be generated based on a CT scan of the hardware elements. These CT scans exhibit inherent misalignment and mu-maps generated therefrom are difficult to align with a patient mu-map and with subsequently-acquired PET data.

Inaccurate mu-maps result in PET images which present inaccurate quantitative values. Inaccurate quantification may hinder diagnosis, treatment planning, and treatment evaluation. Systems are desired to efficiently generate improved linear attenuation coefficient maps for use in PET image reconstruction.

DETAILED DESCRIPTION

The following description is provided to enable any person in the art to make and use the described embodiments. Various modifications, however, will remain apparent to those in the art.

In conventional CT, data is acquired in chunks or slices as the object of interest, in this case hardware elements, passes through the system. The movement of the hardware elements may be periodic (i.e., step-and-shoot) or continuous. The CT data of each portion is reconstructed into a portion-specific volume and the volumes are combined together to generate a final volume representing the desired span of the hardware elements. Some hardware (e.g., a patient table) are too large to be captured with a single pass and must be stitched together with multiple CT scans. A mu-map may then be generated from the final volume using known techniques. A mu-map may be referred to as, for example, a "linear attenuation correction map", an "attenuation correction map" and an "attenuation map".

The final volume and the mu-map generated therefrom may suffer from inaccuracies due to misalignments between the portion-specific volumes, especially in the cases require multiple CT scans of the hardware. An operator may attempt to correct the misalignments manually but such correction is time-consuming and error-prone. The present inventors have discovered that these misalignments may result from table displacement occurring between the acquisitions of CT data of the various portions. Embodiments address these and other displacements by using design data of the hardware elements to align the portion-specific CT volumes prior to combination thereof into a final volume. A mu-map generated from such a final volume exhibits improved accuracy.

Figure 1:
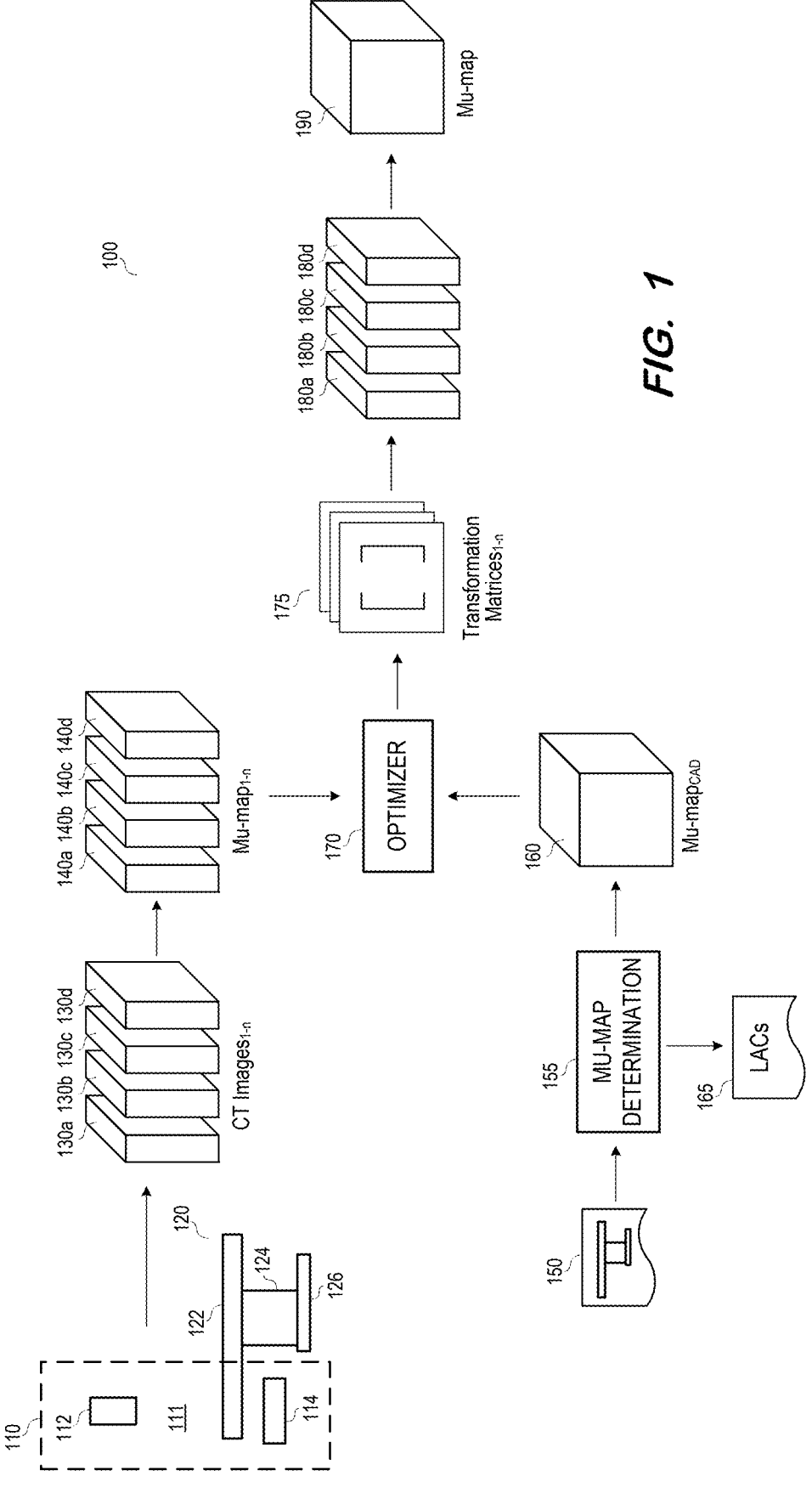
FIG. 1 is a block diagram illustrating generation of a mu-map of hardware elements according to some embodiments.

FIG. 1 is a block diagram of system 100 to generate a mu-map of in-bore hardware elements according to some embodiments. The illustrated components of system 100 may be implemented in computer hardware, in program code and/or in one or more computing systems executing such program code as is known in the art. Such a computing system may include one or more processing units which execute program code stored in one or more non-transitory storage media. More than one functional component may be implemented by a single computing system in some embodiments. One or more of the computing systems may comprise a virtual machine, and one-or more computing systems may comprise a cloud-based compute resource providing on-demand scalability and failure recovery.

Scanner 110 may comprise a CT scanner capable of generating CT data of an object. Embodiments may employ any type of CT scanner, including but not limited to a PET-CT scanner, a SPECT-CT scanner, and a C-Arm scanner.

Scanner 110 includes x-ray source 112 and x-ray detector 114. A CT scanner according to some embodiments may comprise one or more detectors and one or more x-ray sources. Each of the one or more detectors may comprise a photon-counting CT detector or an energy-integrating detector. Generally, CT scanner 110 acquires one or more projection images of objects located in a field of view between x-ray source 112 and x-ray detector 114 at each of various projection angles. In the illustrated example, a first portion of patient table 120 is disposed in the field of view between x-ray source 112 and x-ray detector 114 and therefore the projection images depict the attenuative characteristics of the first portion. A CT image is reconstructed based on the projection images as is known in the art. CT image 130a, for example, represents a three-dimensional volume of the first portion of patient table 120 reconstructed from the projection images acquired while the first portion was disposed between x-ray source 112 and x-ray detector 114.

Table 120 includes support 122, stand 124 and base 126. Support 122 is designed to support a patient during a PET scan. Support 122 may be composed of many individual elements, including but not limited to plastics, composites, metals, wires, circuitry, mechanical components, etc.

Support 122 may be configured to move relative to stand 124 and further into bore 111 to dispose a second portion of table 120 in the field of view between x-ray source 112 and x-ray detector 114. In some embodiments, stand 124 may also or alternatively move relative to base 126 to move support relative to scanner 110. Embodiments are not limited to any particular table configuration or design.

Projection images of the second portion are acquired as described above. CT image 130b represents a three-dimensional volume of the second portion of patient table 120 reconstructed from the projection images acquired while the second portion was disposed between x-ray source 112 and x-ray detector 114. The process may continue as described above until N CT images of adjacent portions of table 122 are reconstructed. FIG. 1 illustrates N=4 CT images 130a through 130d.

Each of CT images 130a-130d is converted to a respective one of mu-maps 140a-140d. The value of each voxel of CT images 130a-130d is converted from Hounsefield units to linear attenuation coefficients as is known in the art. Next, since CT scanners typically use polychromatic x-rays in the ~80-140 keV range, an energy scaling transformation (bilinear or piecewise-linear) is performed to convert the linear attenuation coefficients to 511 keV attenuation coefficients.

FIG. 1 also depicts structural design file 150. File 150 may include a three-dimensional model representing the elements of table 120 (or at least the elements of the relevant portions of table 120). File 150 may define each element in three-dimensional space with respect to each other element, and may indicate a composition (i.e., the materials) of each element. File 150 may represent the elements of table 120 at any suitable resolution and/or level of precision. File 150 may conform to any CAD or other design format.

Mu-map determination component 155 determines mu-map 160 based on file 150 and reference file 165. According to some embodiments, reference file 165 specifies linear attenuation coefficient for each of several materials, including materials specified in file 150. For each element specified in file 150, mu-map determination component 155 determines the linear attenuation coefficients of the materials comprising the element and associates the determined coefficients with the three-dimensional position of the element within table 120. According to some embodiments, file 150 represents the elements of table 120 using polygons. Mu-map determination 155 may therefore convert the polygons to voxels prior to associating the determined coefficients with the voxels.

Optimizer 170 determines transformation matrices 175 based on mu-maps 140a-140d and mu-map 160. Generally, and as will be described in more detail below, optimizer 170 determines a transformation for aligning each of mu-maps 140a-140d with a corresponding portion of mu-map 160. Each transformation matrix 175 is applied to its respective mu-map 140a-140d. Since the corresponding portions of mu-map 160 are aligned with one another, the resulting mu-maps 180a-180d are also aligned with one another. Mu-maps 180a and 180d are combined without requiring further alignment, resulting in mu-map 190 of portions of table 120.

Mu-map 190 may be used to perform attenuation correction of PET data which is (or was) acquired while portions of table 120 are (or were) present in the field of view. Assuming a patient is also present in the field of view during acquisition of the PET data, mu-map 190 may be combined with a mu-map of the patient (e.g., obtained via CT data or MR data) in order to perform attenuation correction.

Figure 2A:
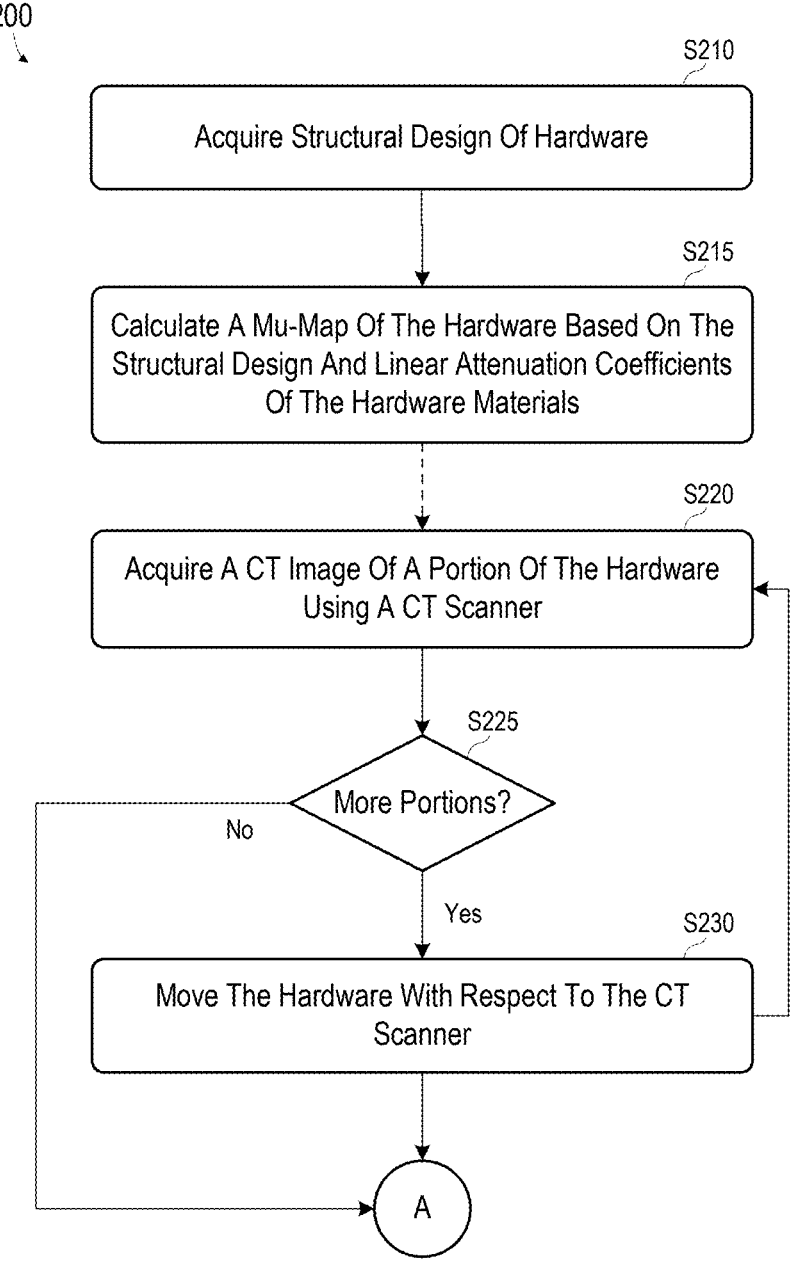
FIGS. 2A and 2B comprise a flow diagram of a process to generate a mu-map of hardware elements according to some embodiments.
Figure 2B:
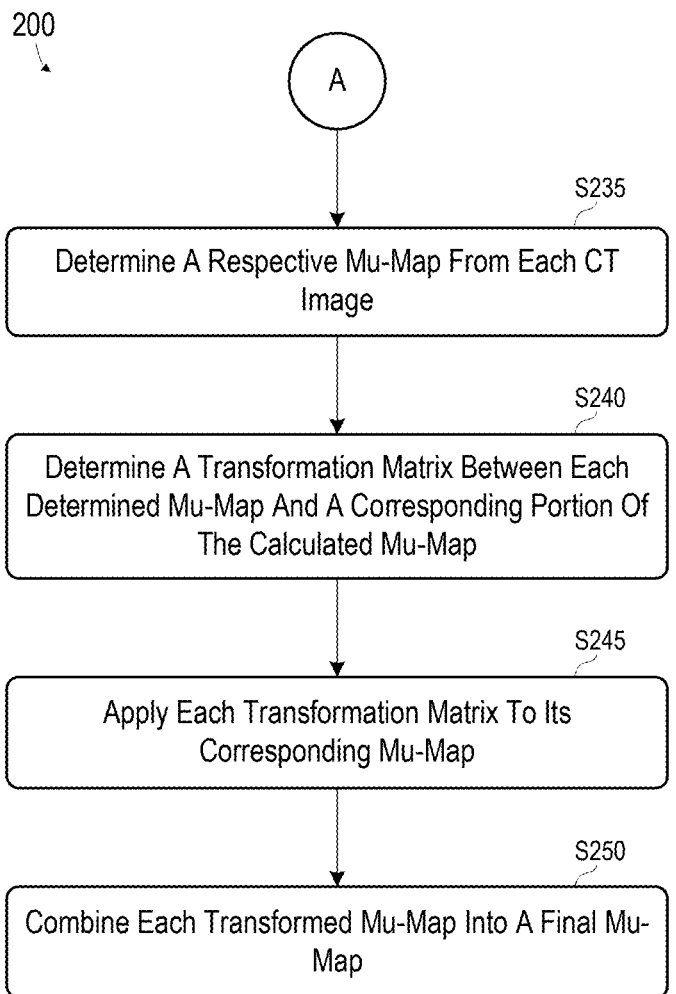

FIGS. 2A and 2B comprise a flow diagram of process 200 to generate a mu-map of hardware elements according to some embodiments. Process 200 may be performed by any combination of hardware and software that is or becomes known. Program code embodying processes described herein may be stored by any one or more non-transitory tangible media, including a fixed disk, a volatile or non-volatile random-access memory, a DVD, a Flash drive, and a magnetic tape, and executed by any suitable processing unit, including but not limited to one or more microprocessors, microcontrollers, processor cores, and processor threads. Embodiments are not limited to the examples described below.

Initially, at S210, a structural design of hardware is acquired. The hardware may consist of physical structures which are expected to be disposed in a field of view during a PET-MR scan. The hardware may include elements of a patient table as described above, and may also include MR coils (e.g., head coil, body coil). The structural design may comprise a three-dimensional model representing the elements of the hardware three-dimensional space with respect to each other element. The design may also specify the material composition of each element. The structural design may be acquired from one or more CAD files such as but not limited to .stl, .dxf, .iges, CATIA, Autodesk inventor and Solid Edge files.

Figure 3:
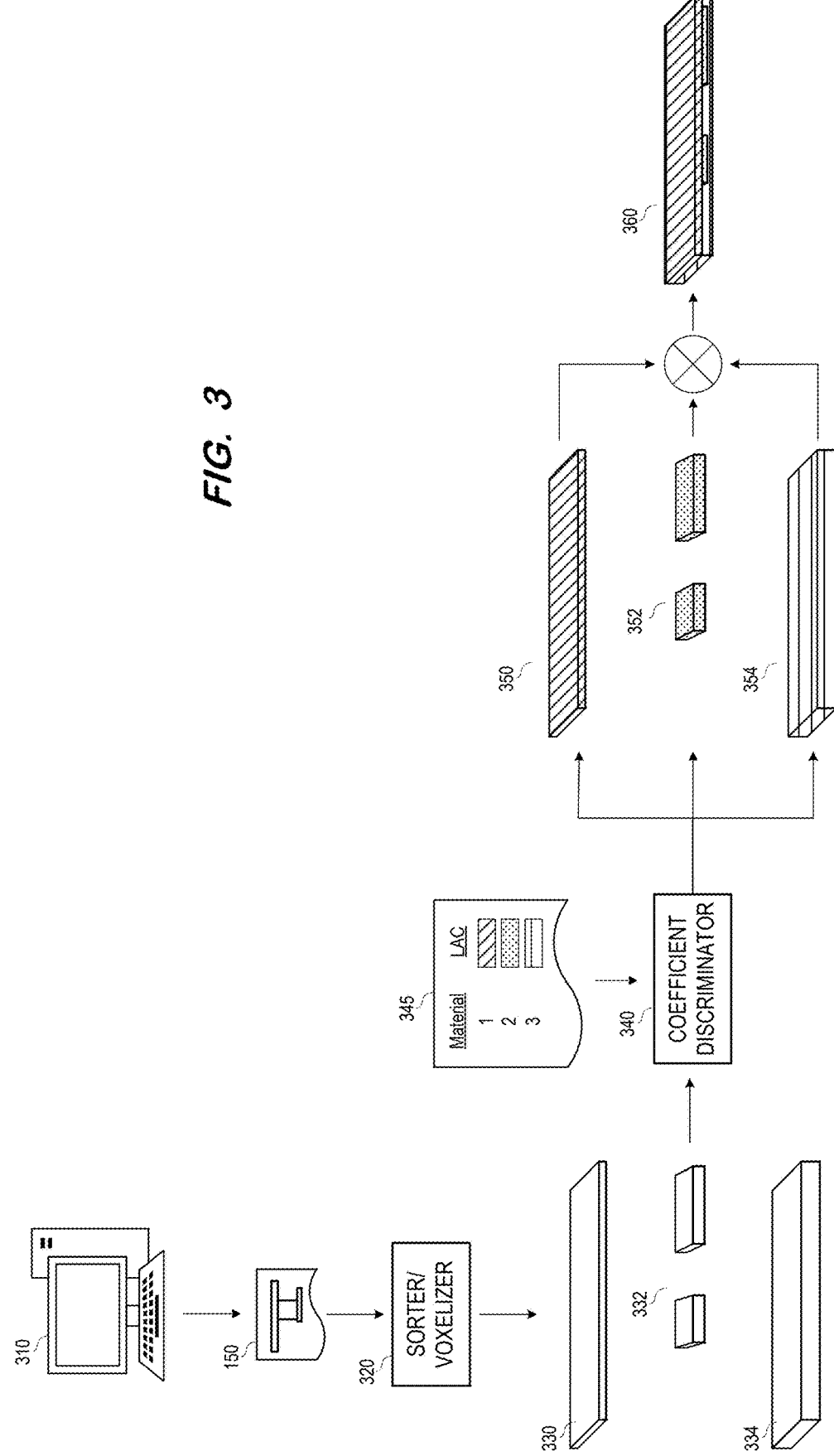
FIG. 3 is a block diagram illustrating calculation of a mu-map of hardware elements according to some embodiments.

A mu-map of the hardware is calculated at S215. The mu-map is calculated based on the structural design and on linear attenuation coefficients of the hardware materials. FIG. 3 is a block diagram illustrating calculation of a mu-map of hardware elements according to some embodiments. FIG. 3 includes computing system 310 which may execute a CAD application, for example. Structural design file 150 is acquired from system 310 at S210.

Sorter/Voxelizer 320 may sort the data of file 150 by material and individually save the sorted data in a CAD format. For example, a file plastic.stl includes CAD data of plastic elements of the table, a file copper.stl includes CAD data of copper elements of the table, and a file fiberglass.stl includes CAD data of fiberglass elements of the table.

Each of the files may represent the hardware elements using polygons. Sorter/Voxelizer 320 converts each file from polygons to voxels, resulting in images 330, 332 and 334. The resolution of images 330, 332 and 334 may be the same as that of a CT image to be acquired at S220. Coefficient discriminator 340 determines one of linear attenuation coefficients 345 for each image 330, 332 and 334 and assigns the linear attenuation coefficients determined for an image to each voxel of the image. The resulting images are depicted in FIG. 3 as images 350, 352 and 354. According to some embodiments, material-specific linear attenuation coefficient images are combined by summing the values of their voxels, resulting in calculated mu-map 360. Any other type of combination may be used at S215.

Figure 4A:
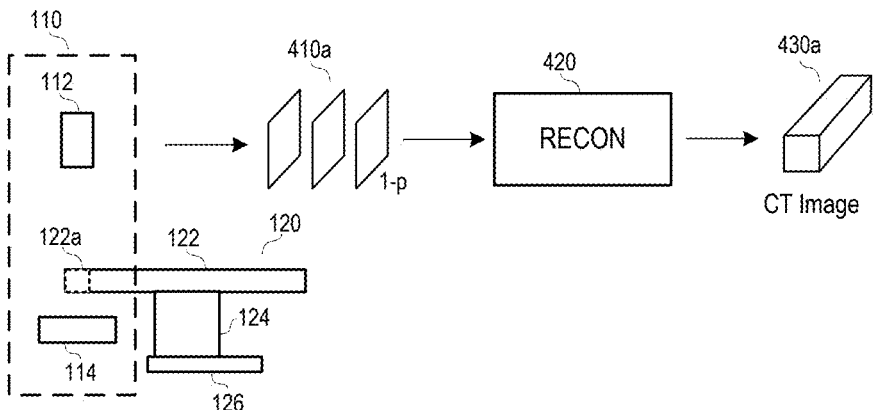
FIGS. 4A through 4C illustrate acquisition of CT images of hardware elements according to some embodiments.
Figure 4B:
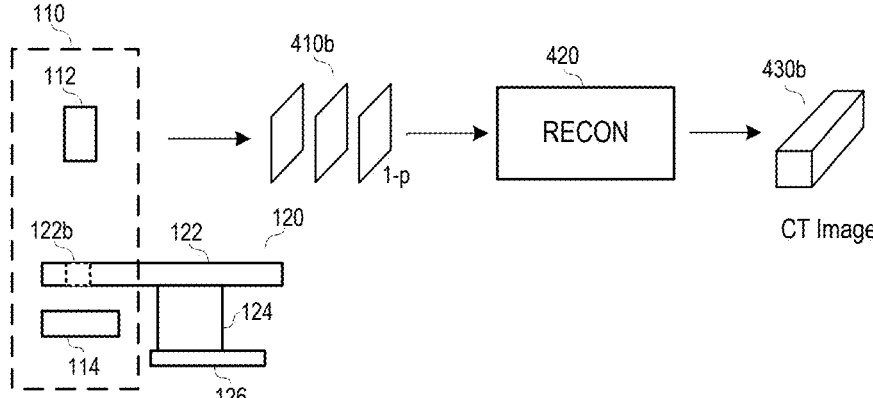
Figure 4C:
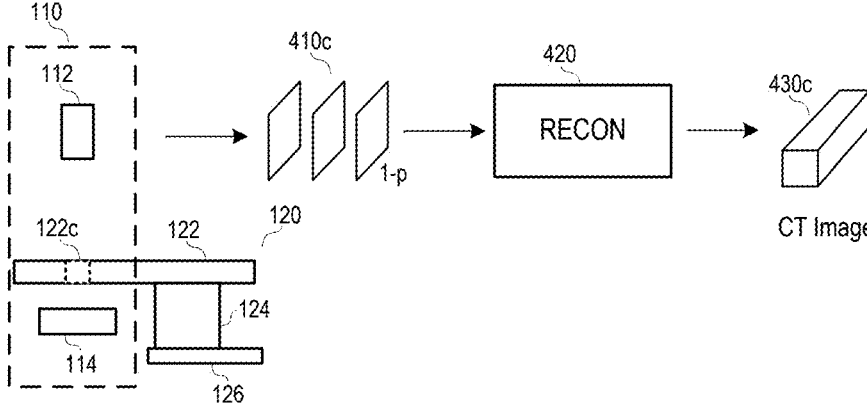

A CT image of a portion of the hardware is acquired using a CT scanner at S220. As indicated by the dashed arrow of FIG. 2A, the CT image may be acquired well after and/or in a different location from calculation of the mu-map at S215. FIGS. 4A through 4C illustrate acquisition of CT images of hardware portions according to some embodiments.

As shown in FIG. 4A, first portion 122a of patient table 120 is positioned in the field of view between x-ray source 112 and x-ray detector 114 of CT scanner 110. In a case that the hardware for which the mu-map was calculated includes one or more MR coils, the one or more MR coils are placed on table 120 in a position anticipated for a PET scan during S220. X-ray source 112 and x-ray detector 114 are rotated around portion 122a to acquire projection images 410a from P projection angles with respect to portion 122a. Reconstruction unit 420 reconstructs three-dimensional CT image 430a of portion 122a from projection images 410a.

Returning to process 200, it is determined at S225 whether images of additional portions of the hardware are to be acquired. If so, the hardware is moved with respect to the CT scanner to dispose another portion of the hardware in the field of view of the CT scanner. FIG. 4B depicts portion 122b of table 120 having been moved between tube 112 and detector 114. Returning to S220, x-ray source 112 and x-ray detector 114 are rotated around portion 122b to acquire projection images 410b and reconstruction unit 420 reconstructs three-dimensional CT image 430b of portion 122b from projection images 410b.

It is assumed that the determination at S225 is again positive and table 120 is moved to place portion 122c between tube 112 and detector 114 as shown in FIG. 4C. Projection images 410c are acquired at S220 and reconstruction unit 420 reconstructs three-dimensional CT image 430c of portion 122c from projection images 410c. It will now be assumed that the determination at S225 is negative (i.e., all needed portions have been acquired) and flow proceeds to S235.

Figure 5A:
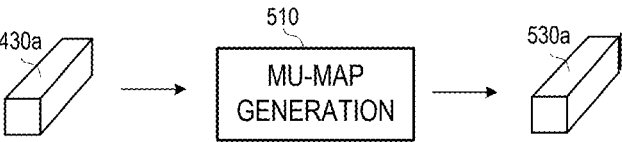
FIGS. 5A through 5C illustrate generation of mu-maps based on CT images of hardware elements according to some embodiments.
Figure 5B:
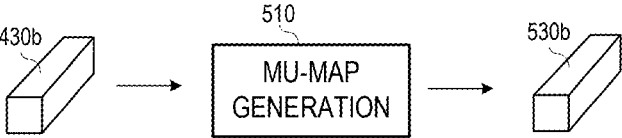
Figure 5C:
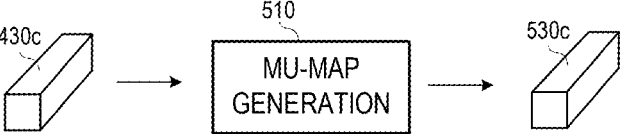

Each CT images acquired at S220 is converted to a respective mu-map at S235. FIGS. 5A through 5C illustrate generation of mu-maps at S235 based on CT images of hardware elements according to some embodiments. Mu-map generation component 510 converts the value of each voxel of CT images 430a-430c from Hounsefield units to linear attenuation coefficients as is known in the art and performs an energy scaling transformation to convert the linear attenuation coefficients to 511 keV attenuation coefficients, resulting in respective mu-maps 530a, 530b and 530c.

Figure 6:
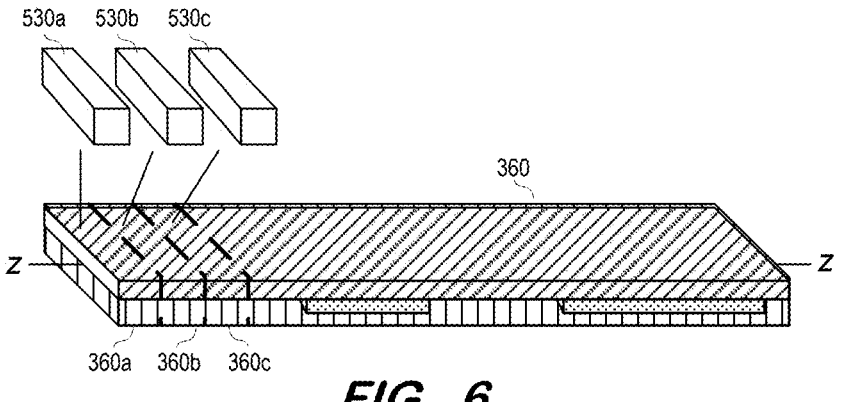
FIG. 6 illustrates correspondences between mu-maps generated based on CT images of hardware elements and portions of a calculated mu-map of the hardware elements according to some embodiments.

Each mu-map determined at S235 corresponds to a portion of the calculated mu-map of S215 which spans the same range of the z-axis. FIG. 6 illustrates mu-maps 530a, 530b and 530c and corresponding portions 360a, 360b and 360c of calculated mu-map 360 according to some embodiments. Due to displacements (e.g., roll, pitch, yaw) of table 120 between acquisitions of the CT images at S220, CT images 430a, 430b, and 430c may be misaligned with one another. As a result, mu-maps 530a, 530b and 530c determined therefrom may also be misaligned with each other. However, corresponding portions 360a, 360b and 360c of calculated mu-map 360 are aligned with one another. Accordingly, aligning each of mu-maps 530a, 530b and 530c with its corresponding portion 360a, 360b or 360c will effectively align mu-maps 530a, 530b and 530c with one another.

Figure 7A:
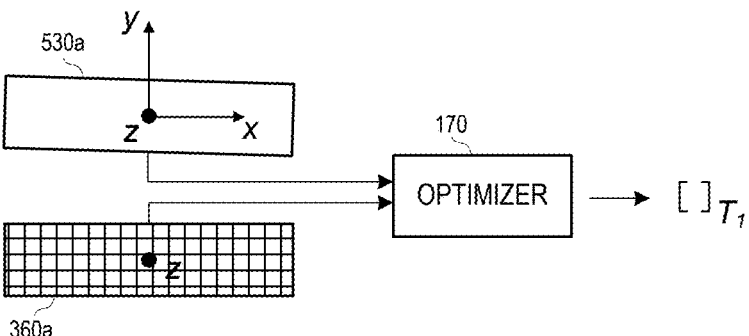
FIGS. 7A through 7C illustrate determination of transformations between mu-maps generated based on CT images of hardware elements and corresponding portions of a calculated mu-map of the hardware elements according to some embodiments.
Figure 7B:
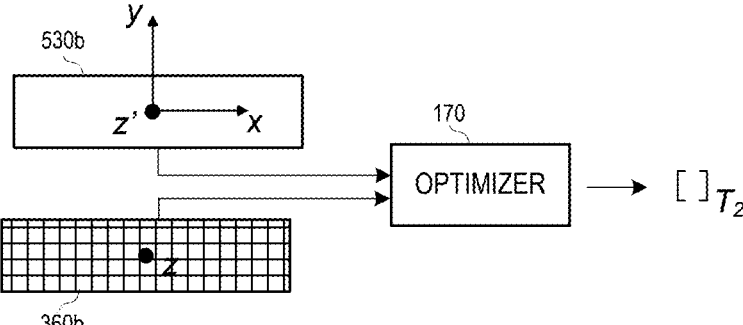
Figure 7C:
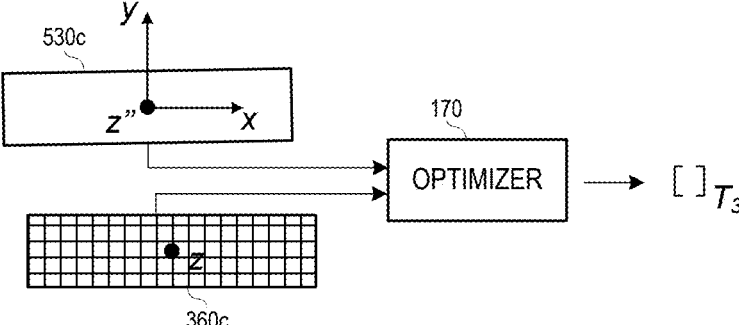

At S240, a transformation matrix is determined between each determined mu-map and a corresponding portion of the mu-map which was calculated at S215. The transformation matrix determined for a mu-map is intended to align the mu-map with its corresponding portion of the calculated mu-map. FIGS. 7A through 7C illustrate determination of transformation matrices at according to some embodiments.

Mu-map 530a is rotated in the x-y plane with respect to portion 360a. Mu-map 530b is shifted in the x-direction with respect to portion 360b, and mu-map 530c is both rotated in the x-y plane and shifted in the x-direction and the y-direction with respect to portion 360c. Optimizer 170 determines transformation matrices $T_1$, $T_2$ and $T_3$ by comparing mu-map 530a to portion 360a, mu-map 530b to portion 360b and mu-map 530c to portion 360c. Optimizer 170 may determine values for each of six degrees of freedom (i.e., x, y, z, roll, pitch, yaw) for a transformation matrix of a given mu-map by independently varying the parameters until the sum of voxel differences between the mu-map and the corresponding CAD-derived mu-map portion is minimized.

Advantageously, the foregoing technique allows optimizer 170 to determine a suitable transformation matrix even if the linear attenuation coefficients of the CAD-derived mu-map portion do not precisely match (or even reflect the same scale as) the linear attenuation coefficients of the CT-derived mu-map portions. Suitable transformation matrices may be determined despite significant discrepancies in the linear attenuation coefficients of voxel representing PCBs and cables in the table or local MR coils, which are difficult to compute with CAD data, as long as the data correlates well for the majority of voxels.

Figure 8A:
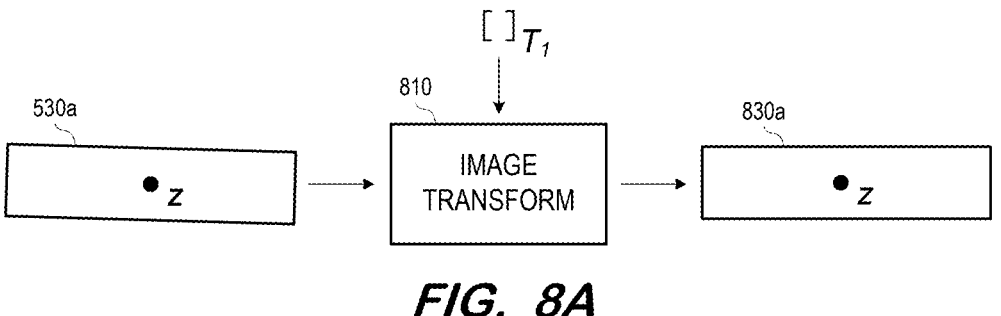
FIGS. 8A through 8C illustrate application of transformations to mu-maps generated based on CT images of hardware elements according to some embodiments.
Figure 8B:
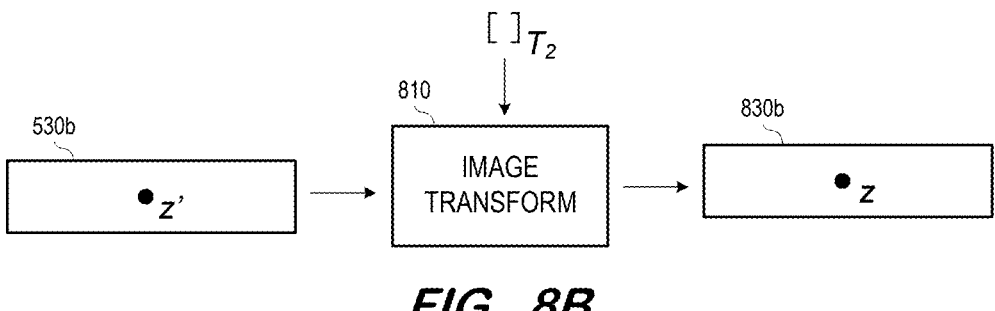
Figure 8C:
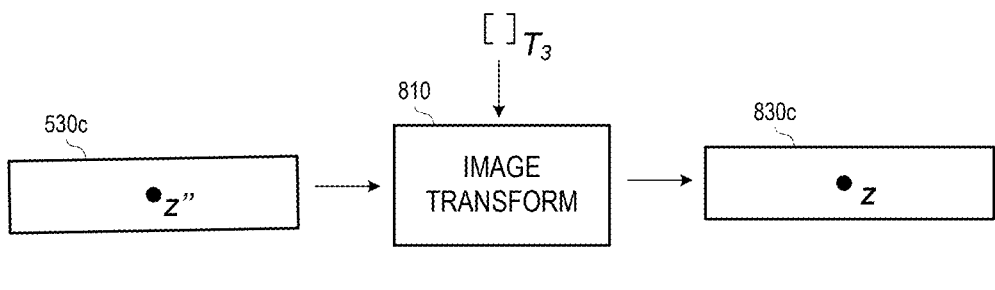
Figure 9:
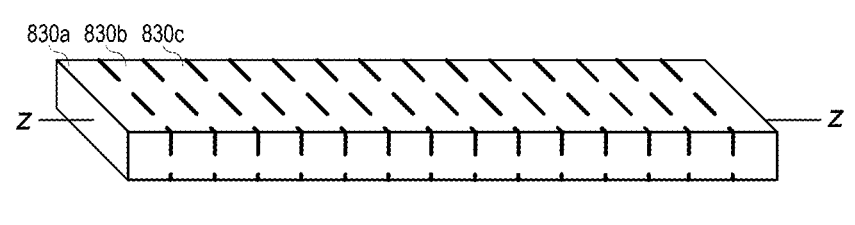
FIG. 9 illustrates combination of transformed mu-maps into a hardware mu-map according to some embodiments.

Each determined transformation matrix is applied to its respective mu-map at S245. FIGS. 8A through 8C illustrate image transform component 810 applying transformation matrices $T_1$, $T_2$ and $T_3$ to mu-maps 530a, 530b and 530c, respectively, resulting in mu-maps 830a, 830b and 830c. Since corresponding portions 360a, 360b and 360c are aligned with each other, mu-maps 830a, 830b and 830c are also aligned with one another. The thusly-aligned mu-maps are combined into a final mu-map at S250. FIG. 9 illustrates hardware mu-map 900 resulting from a combination of aligned mu-maps 830a, 830b, 830c and other aligned mu-maps according to some embodiments.

According to some embodiments, S235 is not executed and the transformation matrices are determined from and applied to CT images 430a, 430b and 430c. Mu-maps are then determined from each of the thusly-transformed CT images 430a, 430b and 430c and combined at S250.

Figure 10:
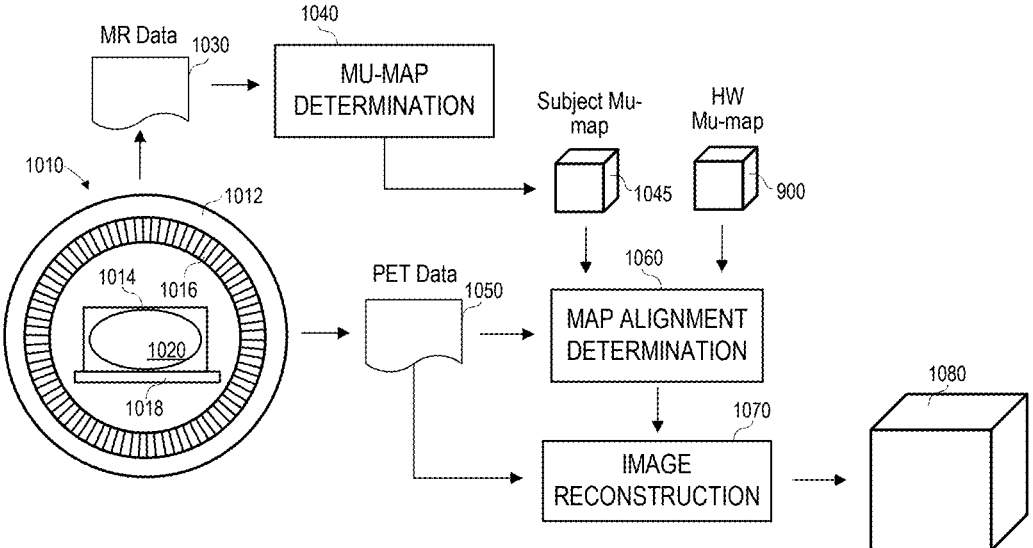
FIG. 10 is a block diagram of a PET-MR system to reconstruct a PET image based on a hardware mu-map according to some embodiments.

Mu-map 900 may be used in the reconstruction of a PET image from PET data according to some embodiments. FIG. 10 is a block diagram of a PET-MR system to reconstruct a PET image based on a hardware mu-map according to some embodiments. FIG. 10 includes an axial view of PET-MR imaging system 1010, which may generate MR images and PET images of imaging subject 1020 disposed therein as is known in the art. Imaging subject 1020 may comprise a human body, a phantom, or any other suitable subject.

PET-MR imaging system 1010 includes housing 1012 comprising MR imaging components (not shown). The MR imaging components may operate in conjunction with one or more MR imaging hardware accessories 1014 disposed within a bore of housing 1012 and adjacent to subject 1020 to generate and acquire MR signals from which an MR image of subject 1020 may be generated. Housing 1012 also includes PET detector ring 1016 and other components required to generate PET data from which a PET image may be reconstructed. Detector ring 1016 may be composed of any number of (e.g., eight) adjacent and coaxial rings of detectors.

PET-MR system 1010 also includes table 1018 on which subject 1020 rests during imaging. As described above, photons emitted from subject 1020 during PET imaging may be attenuated by MR imaging hardware accessories 1014 and table 1018 prior to detection by PET detector ring 1016. It would therefore be beneficial to correct the resulting PET data using one or more attenuation correction maps which represent MR imaging hardware accessories 1014 and table 1018 and are aligned with the PET imaging components. However, since MR imaging hardware accessories 1014 and table 1018 are substantially invisible to the MR imaging components of system 1010, such attenuation correction maps cannot be generated from MR signals acquired by the MR imaging components while subject 1020 is disposed in the desired PET imaging position.

The photons emitted from within subject 1020 are also attenuated by subject 1020 prior to reaching detector ring 1016. Accordingly, as shown in FIG. 10, some embodiments operate to acquire MR data 1030 representing subject 1020 and to generate subject mu-map 1045 based on MR data 1030. Attenuation map determination component 1040 may generate subject mu-map 1045 based on MR data 1030 as is known in the art.

FIG. 10 also shows hardware mu-map 900 which may have been generated as described herein. Mu-map 900 includes linear attenuation coefficients for voxels of table 1018 and any hardware accessories located within the PET field of view of PET-MR system 1010. The PET imaging components of PET-MR system 1010 also operate to generate PET data 1070 based on photons emitted from within subject 1020 as is known in the art.

Generally, each PET detector of detector ring 1016 includes one or more scintillation elements and one or more electrical transducers. In response to receiving 511 keV photons which result from annihilation events within subject 1020, the scintillation elements generate photons having an energy of a few electron volts (eV). The electrical transducers convert the low-energy photons created by the scintillation elements to electrical signals. According to some embodiments, the electrical transducers may comprise, for example, SiPMs, PMTs, or semiconductor-based detectors.

PET data 1050 may represent detected coincidences as raw (i.e., list-mode) data and/or sinograms. List-mode data may represent each coincidence using data specifying a LoR between two crystals, the time at which each photon of the annihilation reached each crystal, the photon energies, etc. A sinogram is a data array of the angle versus the displacement of the LoRs of each detected coincidence. A sinogram includes one row containing the LoR for a particular azimuthal angle φ. Each of these rows corresponds to a one-dimensional parallel projection of the tracer distribution at a different coordinate. A sinogram stores the location of the LoR of each coincidence such that all the LoRs passing through a single point in the volume trace a sinusoid curve in the sinogram.

A "true" coincidence represents the detection of two coincident photons which arose from a single annihilation event located on a LoR between the two detectors. A "random" coincidence represents two coincident photons which did not arise from the same annihilation event. A "scatter" coincidence is a type of true coincidence in which two coincident photons originated from the same annihilation event but the annihilation event was not located along the LoR of the two detectors because one or both of the photons interacted and scattered within the body or with other material.

Conventional PET scanners detect all coincidences without regard to whether the coincidences are true, random or scatter coincidences. Since only the true coincidences represent spatial information regarding the distribution of the tracer within the body, random coincidences and scatter coincidences are often subtracted from or otherwise used to correct acquired PET data before or during reconstruction of a PET image. Software and/or hardware-based approaches can be used to estimate random coincidences and to subtract the random coincidences from the detected coincidences to result in PET data 1050.

Map alignment determination component 1060 receives subject mu-map 1045, hardware mu-map 900 and PET data 1050. Map alignment determination component 1060 operates to determine an alignment (and/or distortion) of hardware mu-map 900 with respect to PET data 1050. According to some embodiments, the determined alignment is intended to result in more accurate attenuation correction of PET data 1050 than current techniques. Determination of the alignment and/or distortion may comprise determination of an alignment and/or distortion of hardware mu-map 900 which, when used to attenuation-correct PET data 1050, maximizes a consistency of thusly-corrected PET data 1050.

Image reconstruction component 1070 receives PET data 1050, aligned hardware mu-map 900 and subject mu-map 1045, and reconstructs PET image 1080 based thereon. Image reconstruction component 1070 may employ any reconstruction algorithm that is or becomes known. Such a reconstruction algorithm may correct PET data 1050 for random and scatter coincidences, and based on the received mu-maps, prior to or during reconstruction.

Figure 11:
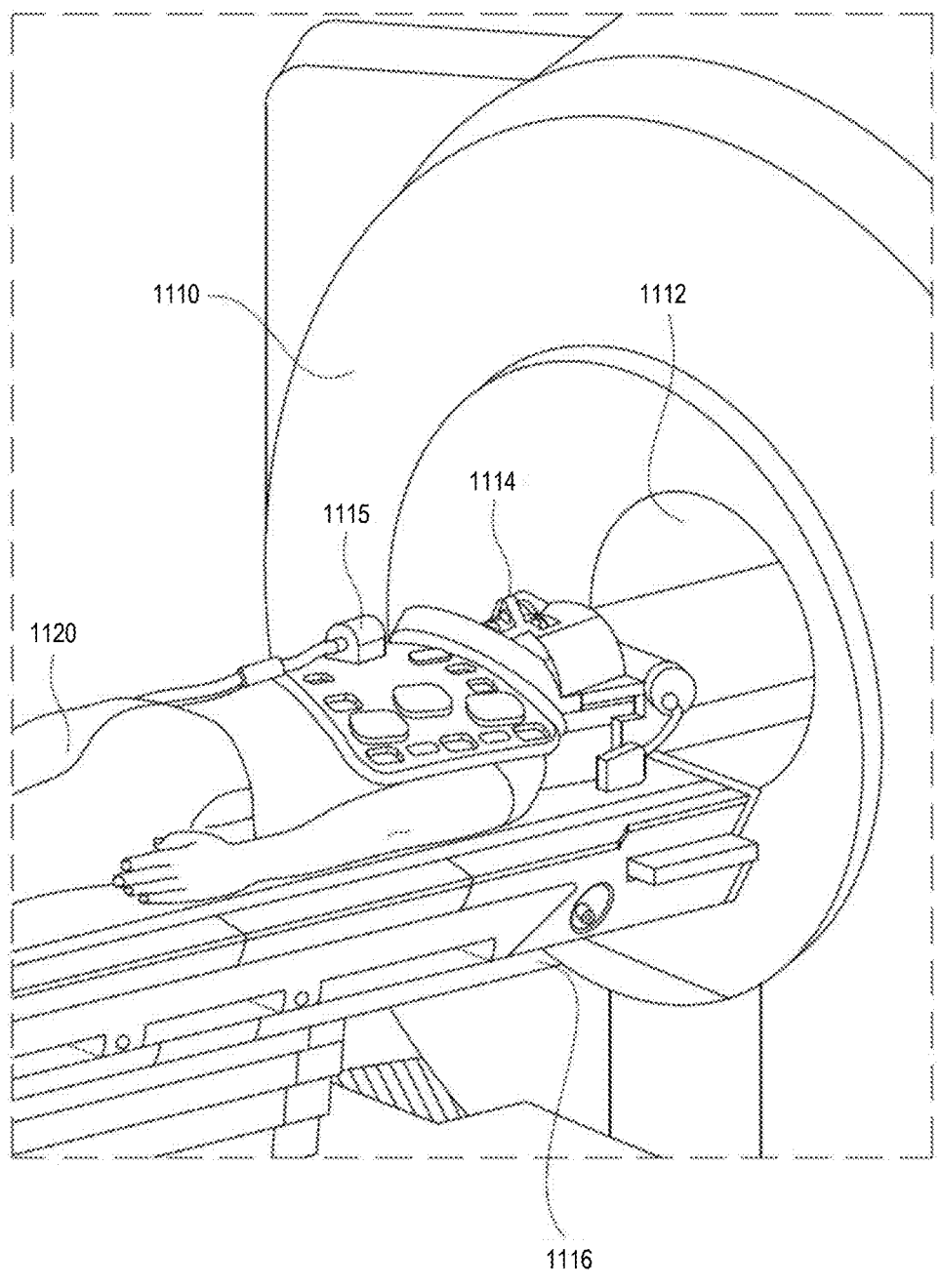
FIG. 11 is a view of a PET-MR system prior to scanning a patient, a head/neck coil and a body coil according to some embodiments.

FIG. 11 shows subject 1120 prior to being placed into bore 1112 of PET-MR system housing 1110. MR head/neck coil 1114 and MR body coil 1115 surround subject 1120 and will therefore be disposed in the field of view of a subsequent PET scan. Accordingly, S215 of process 200 may include calculation of a mu-map based on a structural design of MR head/neck coil 1114, MR body coil 1115 and table 116 and of an attenuation correction map associated with MR head/neck coil 1114 and the CT images acquired at S220 may include various portions of MR head/neck coil 1114, MR body coil 1115 and/or table 1116.

Figure 12:
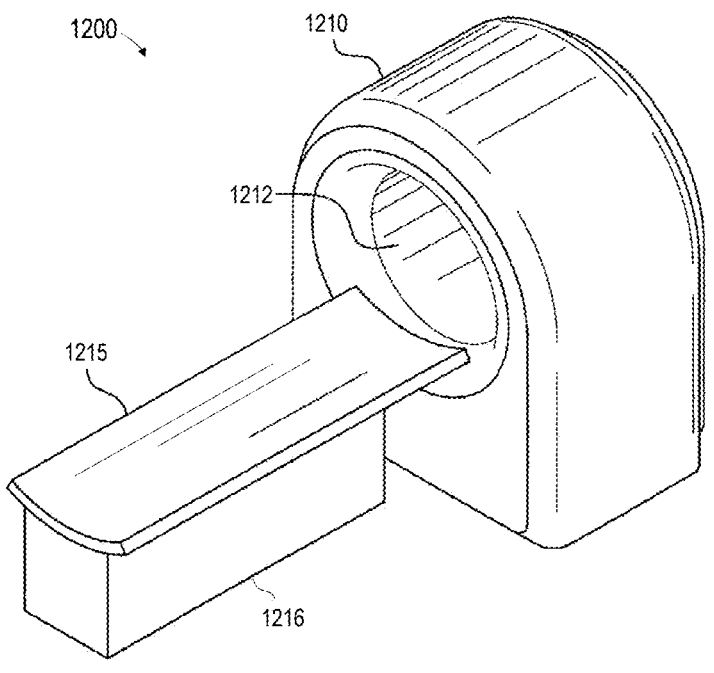
FIG. 12 is a block diagram of a CT imaging system according to some embodiments.
Figure 12:
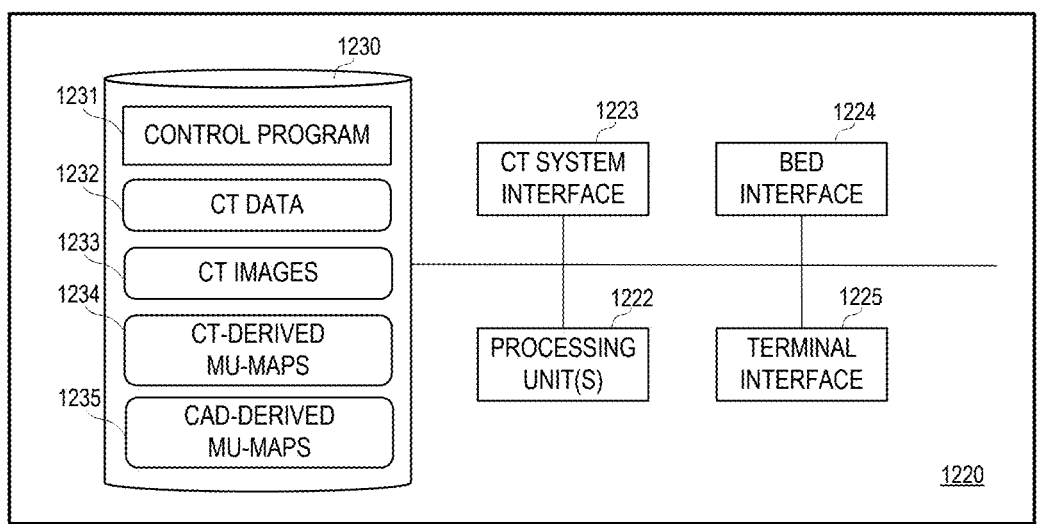
Figure 12:
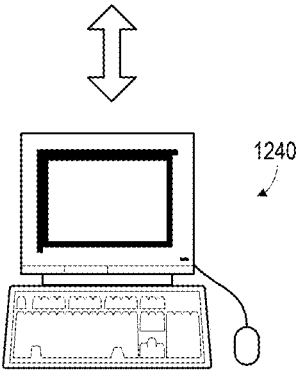

FIG. 12 illustrates CT scanner 1200 to execute one or more of the steps described herein. Embodiments are not limited to scanner 1200. Scanner 1200 includes gantry 1210 defining bore 1212. Gantry 1210 includes CT imaging components for acquiring CT image data of objects (e.g., a patient, a table, MR coils) disposed in bore 1212. The CT imaging components may include one or more x-ray tubes and one or more corresponding detectors as is known in the art.

Bed 1215 and base 1216 are operable to move a patient lying on bed 1215 into and out of bore 1212 before, during and after imaging. In some embodiments, bed 1215 is configured to translate over base 1216 and, in other embodiments, base 1216 is movable along with or alternatively from bed 1215. Bed 1215 and base 1216 may provide continuous bed motion and/or step-and-shoot motion during such scanning according to some embodiments.

Control system 1220 may comprise any general-purpose or dedicated computing system. Control system 1220 includes one or more processing units 1222 (e.g., processors, processor cores, execution threads, etc.) configured to execute program code to cause system 1220 to acquire CT data and generate images therefrom, and storage device 1230 for storing the program code. Storage device 1230 may comprise one or more fixed disks, solid-state random-access memory, and/or removable media (e.g., a thumb drive) mounted in a corresponding interface (e.g., a Universal Serial Bus port).

Storage device 1230 stores program code of control program 1231. One or more processing units 1222 may execute control program 1231 to control CT imaging elements of scanner 1200 using CT system interface 1223 and bed interface 1224 to acquire CT data 1232 of hardware disposed in bore 1212 and to reconstruct CT images 1233 therefrom. Mu-maps 1234 may be derived from CT data 1232. Mu-maps 1235 may be derived from CAD data of the hardware disposed in bore 1212 as described herein. Moreover, control program 1231 may be executed as described herein to align mu-maps 1234 with corresponding portions of mu-maps 1235 and to combine the aligned mu-maps into a mu-map of the hardware for use in future PET reconstruction.

CT images 1233, mu-maps 1234 and mu-maps 1235 may be transmitted to terminal 1240 via terminal interface 1226. Terminal 1240 may comprise a display device and an input device coupled to system 1220. Terminal 1240 may display the received CT images 1233, mu-maps 1234 and mu-maps 1235. Terminal 1240 may receive user input for controlling display of the data, operation of scanner 1200, and/or the processing described herein. In some embodiments, terminal 1240 is a separate computing device such as, but not limited to, a desktop computer, a laptop computer, a tablet computer, and a smartphone.

Figure 13:
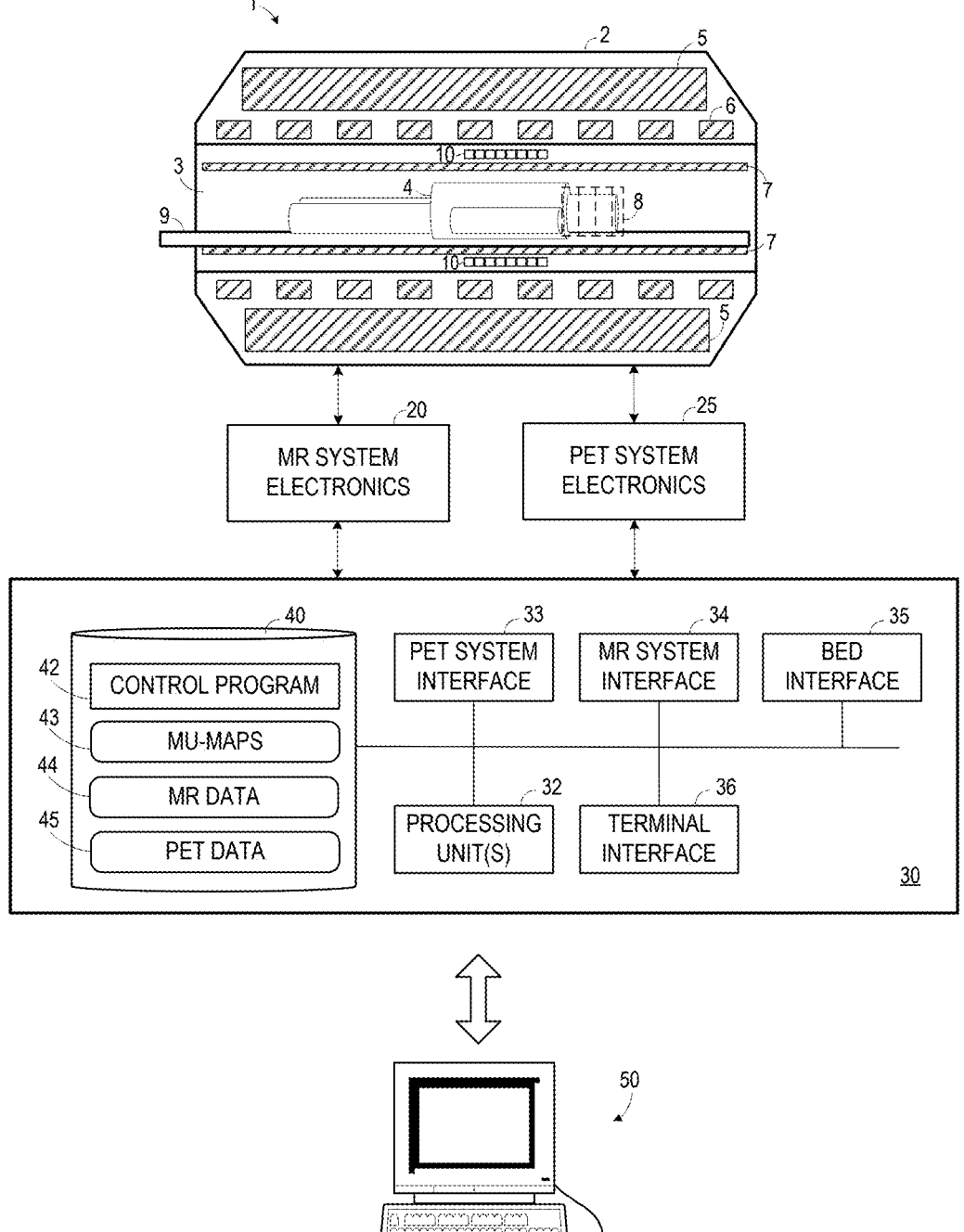
FIG. 13 is a block diagram of a PET-MR imaging system according to some embodiments.

FIG. 13 illustrates PET-MR system 1 for executing MR and PET scans according to some embodiments. System 1 includes chassis 2, which defines bore 3 in which patient 4 is disposed. Chassis 2 includes polarizing main magnet 5, gradient coils 6 and RF coil 7 arranged about bore 3. MR head/neck coil 8 is disposed about a head and neck of patient 4 According to some embodiments, polarizing main magnet 5 generates a uniform main magnetic field ($B_0$), gradient coils 6 produce magnetic field gradients $G_x$, $G_y$, and $G_z$ to select particular portions of patient 4 to image, RF coil 7 emits an excitation field ($B_1$), and MR head/neck coil 8 receives signals emitted from patient 4 after removal of the excitation field.

PET detectors 10 comprise a ring of PET detectors disposed between gradient coils 6 and RF coil 7, but embodiments are not limited thereto. PET detectors 10 may include any number or type of detectors in any configuration as is known in the art. Each detector may include one or more scintillation elements and one or more electrical transducers to generate an electrical signal in response to a received gamma photon.

System 30 controls operation of PET-MR system 1 via MR system electronics 20 and PET system electronics 25. MR system electronics 20 may comprise, for example, sequence controllers, digital-analog converters and power amplifiers to generate gradient pulses and RF pulses according to a desired MR imaging sequence. PET system electronics 25 may comprise electronic components to receive electrical signals generated by detectors 10 and detect coincidences based thereon.

System 30 may comprise any general-purpose or dedicated computing system. System 30 of FIG. 13 includes one or more processing units 32 configured to execute processor-executable program code to cause system 30 to operate as described herein, and storage device 40 for storing the program code. Storage device 40 may comprise one or more fixed disks, solid-state random-access memory, and/or removable media (e.g., a thumb drive) mounted in a corresponding interface (e.g., a USB port).

Storage device 40 stores program code of control program 42. One or more processing units 32 may execute control program 42 to provide instructions to MR system electronics 20 via MR system interface 34. For example, control program 42 may be executed to instruct MR system electronics 20 to initiate a desired pulse sequence in order to acquire MR data for storage within MR data 44. Control program 42 may also be executed to instruct PET system electronics 25 to acquire PET data 45 representing coincidences acquired by PET detectors 10. Control program 42 may further include processor-executable program code to cause system 30 to perform attenuation correction on acquired PET data based on a hardware mu-map 43 generated as described herein and on a mu map 43 of patient 4 generated based on MR data 44.

Acquired and/or attenuation-corrected PET, MR and combined images may be provided to terminal 50 via terminal interface 36 of system 30. Terminal interface 36 may also receive input from terminal 50, which may be used to provide commands to control program 42 in order to control elements of system 1. The commands may include commands to initiate an imaging sequence to acquire image data of a subject. Terminal 50 may simply comprise a display device and an input device coupled to system 30. In some embodiments, terminal 50 is a separate computing device such as, but not limited to, a desktop computer, a laptop computer, a tablet computer, and a smartphone.

Each component described herein may include any elements which are necessary for the operation thereof, as well as additional elements for providing functions other than those described herein. Each functional component described herein may be implemented in computer hardware, in program code and/or in one or more computing systems executing such program code as is known in the art. Such a computing system may include one or more processing units which execute processor-executable program code stored in a memory system.

Those in the art will appreciate that various adaptations and modifications of the above-described embodiments can be configured without departing from the claims. Therefore, it is to be understood that the claims may be practiced other than as specifically described herein.

What is claimed is:

1. A system comprising:

an x-ray tube;

a detector to receive photons emitted by the x-ray tube and generate respective projection data based on the received photons;

a processing unit to:

operate the x-ray tube and the detector to generate respective projection data of each of a plurality of portions of a patient support;

reconstruct a respective computed tomography (CT) image of each of the plurality of portions from the respective projection data of each of the plurality of portions;

generate a respective linear attenuation coefficient map of each of the plurality of portions from the respective CT image;

determine a respective transformation matrix between each of the linear attenuation coefficient maps and a corresponding portion of a predetermined linear attenuation coefficient map of the patient support;

apply the respective transformation matrix to each of the linear attenuation coefficient maps; and combine the transformed linear attenuation coefficient maps.

2. The system of claim 1, wherein the predetermined linear attenuation coefficient map of the patient support is calculated based on a structural design of the patient support, materials of the patient support, and linear attenuation coefficients of the materials.

3. The system of claim 2, wherein the structural design is specified in a computer-aided design file.

4. The system of claim 2, wherein determination of a respective transformation matrix between each of the linear attenuation coefficient maps and a corresponding portion of a predetermined linear attenuation coefficient map of the patient support comprises:

determination, for each of the linear attenuation coefficient maps, of an (x, y, z) position and a rotation angle around each of x, y and z axes relative to the corresponding portion of the predetermined linear attenuation coefficient map.

5. The system of claim 2, wherein a scale of the predetermined linear attenuation coefficient map is different from a scale of the plurality of linear attenuation coefficient maps.

6. The system of claim 1, wherein determination of a respective transformation matrix between each of the linear attenuation coefficient maps and a corresponding portion of a predetermined linear attenuation coefficient map of the patient support comprises:

determination, for each of the linear attenuation coefficient maps, of an (x, y, z) position and a rotation angle around each of x, y and z axes relative to the corresponding portion of the predetermined linear attenuation coefficient map.

7. The system of claim 6, wherein a scale of the predetermined linear attenuation coefficient map is different from a scale of the plurality of linear attenuation coefficient maps.

8. A method comprising:

acquiring a respective computed tomography (CT) image of each of a plurality of adjacent portions of a patient support;

determining a respective transformation matrix between each of the CT images and a corresponding portion of a predetermined linear attenuation coefficient map of the patient support;

applying the respective transformation matrix to each of the CT images;

generating a respective linear attenuation coefficient map from each of the transformed CT images;

combining the linear attenuation coefficient maps into a combined linear attenuation coefficient map; and reconstructing a positron emission tomography (PET) image based on PET data and the combined linear attenuation coefficient map.

9. The method of claim 8, further comprising:

calculating the predetermined linear attenuation coefficient map of the patient support based on a structural design of the patient support, materials of the patient support, and linear attenuation coefficients of the materials.

10. The method of claim 9, further comprising determining the structural design from a computer-aided design file.

11. The method of claim 9, wherein determining a respective transformation matrix between each of the CT images and a corresponding portion of the predetermined linear attenuation coefficient map of the patient support comprises:

determining, for each of the CT images, an (x, y, z) position and a rotation angle around each of x, y and z axes relative to the corresponding portion of the predetermined linear attenuation coefficient map.

12. The method of claim 9, wherein the predetermined linear attenuation coefficient map comprises values of linear attenuation coefficients and a plurality of CT images comprise Hounsfield values.

13. The method of claim 12, wherein the predetermined linear attenuation coefficient map comprises values of linear attenuation coefficients and the plurality of CT images comprise Hounsfield values.

14. The method of claim 8, wherein determining a respective transformation matrix between each of the CT images and a corresponding portion of a predetermined linear attenuation coefficient map of the patient support comprises:

determining, for each of the CT images, an (x, y, z) position and a rotation angle around each of x, y and z axes relative to the corresponding portion of the predetermined linear attenuation coefficient map.

15. One or more non-transitory computer-readable media storing program code executable by a processor to cause a system to perform operations comprising:

acquiring a respective computed tomography (CT) image of each of a plurality of adjacent portions of a patient support;

determining a respective transformation matrix between each of the CT images and a corresponding portion of a predetermined linear attenuation coefficient map of the patient support;

applying the respective transformation matrix to each of the CT images;

generating a respective linear attenuation coefficient map from each of the transformed CT images;

combining the linear attenuation coefficient maps into a combined linear attenuation coefficient map; and reconstructing a positron emission tomography (PET) image based on PET data and the combined linear attenuation coefficient map.

16. The one or more non-transitory computer-readable media of claim 15, the program code executable by a processor to cause a system to perform operations further comprising:

calculating the predetermined linear attenuation coefficient map of the patient support based on a structural design of the patient support, materials of the patient support, and linear attenuation coefficients of the materials.

17. The one or more non-transitory computer-readable media of claim 16, the program code executable by a processor to cause a system to perform operations further comprising determining the structural design from a computer-aided design file.

18. The one or more non-transitory computer-readable media of claim 16, wherein determining a respective transformation matrix between each of the CT images and a corresponding portion of the predetermined linear attenuation coefficient map of the patient support comprises:

determining, for each of the CT images, an (x, y, z) position and a rotation angle around each of x, y and z axes relative to the corresponding portion of the predetermined linear attenuation coefficient map.

19. The one or more non-transitory computer-readable media of claim 16, wherein the predetermined linear attenuation coefficient map comprises values of linear attenuation coefficients and a plurality of CT images comprise Hounsfield values.

20. The one or more non-transitory computer-readable media of claim 15, wherein determining a respective transformation matrix between each of the CT images and a corresponding portion of a predetermined linear attenuation coefficient map of the patient support comprises:

determining, for each of the CT images, an (x, y, z) position and a rotation angle around each of x, y and z axes relative to the corresponding portion of the predetermined linear attenuation coefficient map.

* * * * *